United States Patent
Matsui et al.

(10) Patent No.: US 7,625,464 B2
(45) Date of Patent: Dec. 1, 2009

(54) METHOD FOR PRODUCING HEAT-GENERATING FORMED PRODUCT

(75) Inventors: Kunio Matsui, Tochigi (JP); Yoshiaki Kumamoto, Tochigi (JP); Masataka Ishikawa, Tochigi (JP)

(73) Assignee: Kao Corporation, Tokyo (JP)

( * ) Notice: Subject to any disclaimer, the term of this patent is extended or adjusted under 35 U.S.C. 154(b) by 289 days.

(21) Appl. No.: 10/490,120

(22) PCT Filed: Sep. 26, 2002

(86) PCT No.: PCT/JP02/09961

§ 371 (c)(1),
(2), (4) Date: Aug. 30, 2004

(87) PCT Pub. No.: WO03/028597

PCT Pub. Date: Apr. 10, 2003

(65) Prior Publication Data

US 2005/0000827 A1 Jan. 6, 2005

(30) Foreign Application Priority Data

Sep. 28, 2001 (JP) ............................. 2001-304270

(51) Int. Cl.
- A61F 7/08 (2006.01)
- D21J 3/00 (2006.01)

(52) U.S. Cl. ................... 162/218; 162/135; 162/158; 162/181.9; 162/184

(58) Field of Classification Search ................ 162/158, 162/181.1–181.9, 183–184, 134–135, 204–205, 162/218
See application file for complete search history.

(56) References Cited

U.S. PATENT DOCUMENTS

| | | | | |
|---|---|---|---|---|
| 2,033,928 A | * | 3/1936 | Driscoll et al. | 442/101 |
| 2,422,046 A | * | 6/1947 | Ruben | 429/94 |
| 3,907,758 A | * | 9/1975 | Sackmann et al. | 525/157 |
| 4,794,043 A | * | 12/1988 | Kaji et al. | 428/408 |
| 5,039,845 A | * | 8/1991 | Clough et al. | 219/543 |
| 5,317,132 A | * | 5/1994 | Clough et al. | 219/543 |
| 5,425,975 A | * | 6/1995 | Koiso et al. | 428/74 |
| 5,489,492 A | * | 2/1996 | Asami et al. | 429/212 |
| 5,873,909 A | * | 2/1999 | Brodmann et al. | 8/403 |
| 5,975,074 A | * | 11/1999 | Koiso et al. | 126/204 |
| 6,096,223 A | | 8/2000 | El-Shoubary et al. | |
| 6,127,290 A | * | 10/2000 | Koiso et al. | 442/72 |
| 6,127,294 A | * | 10/2000 | Koiso et al. | 442/327 |
| 6,974,470 B2 | * | 12/2005 | Tsunakawa et al. | 607/109 |
| 2002/0081930 A1 | * | 6/2002 | Jackson et al. | 442/416 |
| 2003/0086860 A1 | * | 5/2003 | Uehara et al. | 423/449.2 |
| 2004/0045690 A1 | * | 3/2004 | Eto et al. | 162/225 |
| 2004/0058166 A1 | * | 3/2004 | Nakamura | 428/425.1 |
| 2005/0000827 A1 | * | 1/2005 | Matsui et al. | 205/689 |
| 2005/0028806 A1 | | 2/2005 | Kumamoto et al. | |
| 2005/0192653 A1 | * | 9/2005 | Tsunakawa et al. | 607/109 |
| 2006/0151136 A1 | * | 7/2006 | Kumamoto et al. | 162/158 |
| 2006/0276863 A1 | * | 12/2006 | Kumamoto et al. | 607/96 |
| 2007/0020412 A1 | * | 1/2007 | Kumamoto et al. | 428/34.2 |
| 2007/0110790 A1 | * | 5/2007 | Igaki et al. | 424/443 |
| 2008/0292879 A1 | * | 11/2008 | Kumamoto et al. | 428/339 |
| 2009/0101867 A1 | * | 4/2009 | Ishikawa et al. | 252/183.12 |

FOREIGN PATENT DOCUMENTS

| | | | |
|---|---|---|---|
| CN | 1196671 A | | 10/1998 |
| EP | 0 786 240 A1 | | 7/1997 |
| EP | 0 856 302 A1 | | 8/1998 |
| JP | 1-201253 | | 8/1989 |
| JP | 3-152894 | | 6/1991 |
| JP | 6-158600 | | 6/1994 |
| JP | 06-218273 A | | 8/1994 |
| JP | 7-59809 | | 3/1995 |
| JP | 3155522 | | 2/2001 |
| JP | 2004143232 A | * | 5/2004 |
| JP | 2005224316 A | * | 8/2005 |
| JP | 2005328852 A | * | 12/2005 |
| JP | 2006314618 A | * | 11/2006 |
| WO | 96/11654 | | 4/1996 |
| WO | 98/00077 | | 1/1998 |

OTHER PUBLICATIONS

English Abastract of JP 01-201253, Dated Aug. 14, 1989.*
U.S. Appl. No. 10/566,471, filed Jan. 31, 2006, Kumamoto, et al.
U.S. Appl. No. 10/556,136, filed Nov. 9, 2005, Kumamoto, et al.
English Language Translation of JP 1-201253, Aug. 14, 1989.
U.S. Appl. No. 12/063,476, filed Feb. 11, 2008, Ishikawa, et al.

* cited by examiner

Primary Examiner—José A Fortuna
(74) Attorney, Agent, or Firm—Oblon, Spivak, McClelland, Maier & Neustadt, L.L.P.

(57) ABSTRACT

A process of producing a heat generating molded article comprising the steps of making an intermediate product by a papermaking process from a raw material composition containing at least an oxidizable metal powder, a moisture retaining agent, a fibrous material, and water and incorporating an electrolyte into the resulting intermediate product.

16 Claims, 1 Drawing Sheet

METHOD FOR PRODUCING HEAT-GENERATING FORMED PRODUCT

TECHNICAL FIELD

The present invention relates to a process of producing a molded article capable of generating heat by utilizing heat generation accompanying oxidation of oxidizable metal powder with oxygen in air.

BACKGROUND ART

The process disclosed in JP-A-1-201253 is among known techniques pertinent to production of a heat generating molded article using oxidation reaction of oxidizable metal powder with oxygen in air. According to the process, a raw material slurry is prepared by suspending a fibrous substance in water and adding thereto an oxidizable metal, e.g., iron powder, activated carbon as a moisture retaining agent, an electrolyte as a reaction assistant, etc. A fiber layer prepared from the slurry by a papermaking process is dewatered by suction and pressed into a heat generating molded article of sheet form having a water content of 5 to 65 wt %.

Because the electrolyte has previously been added into the slurry before papermaking, it is difficult to control the electrolyte content in the molded article obtained by papermaking and dewatering. Presence of the electrolyte, which is a reaction assistant, in the slurry can induce oxidation of the oxidizable metal as suspended in the slurry. It is more likely that oxidation of the oxidizable metal has started abruptly by the time when the watery fiber layer is subjected to dewatering and shaping. In order to suppress such an oxidation reaction, it has been necessary to take some countermeasures such as carrying out the production in an inert gas atmosphere, which makes the production equipment complicated.

JP-A-3-152894 discloses a technique comprising the steps of scattering oxidizable metal powder on a sheet substrate made up of irregularly accumulated fibers and having a large number of voids, vibrating the substrate to prepare a sheet structure having the oxidizable metal powder held in the inside of the substrate, and impregnating the structure with an electrolyte solution having activated carbon suspended therein.

According to this technique, however, since the activated carbon is in a suspended state in the electrolyte solution to be infiltrated into the structure, it is not allowed to penetrate deep into the structure. The resulting heat generating article has the oxidizable metal powder, activated carbon, and fiber dispersed therein non-uniformly. As a result, the heat generating article fails to exhibit satisfactory heat generation characteristics.

Accordingly, an object of the present invention is to provide a process of producing a heat generating molded article, which process enables easy control of the electrolyte content in the final product, minimizes the oxidation of the oxidizable metal during the production, and provides a molded article with satisfactory heat generation characteristics.

DISCLOSURE OF THE INVENTION

The above object of the present invention is accomplished by a novel process for producing a heat generating molded article. According to the process, an intermediate product is formed by a papermaking process from a raw material composition containing at least an oxidizable metal powder, a moisture retaining agent, a fibrous material, and water, and an electrolyte is incorporated into the resulting intermediate product.

BEST MODE FOR CARRYING OUT THE INVENTION

Figure 1:
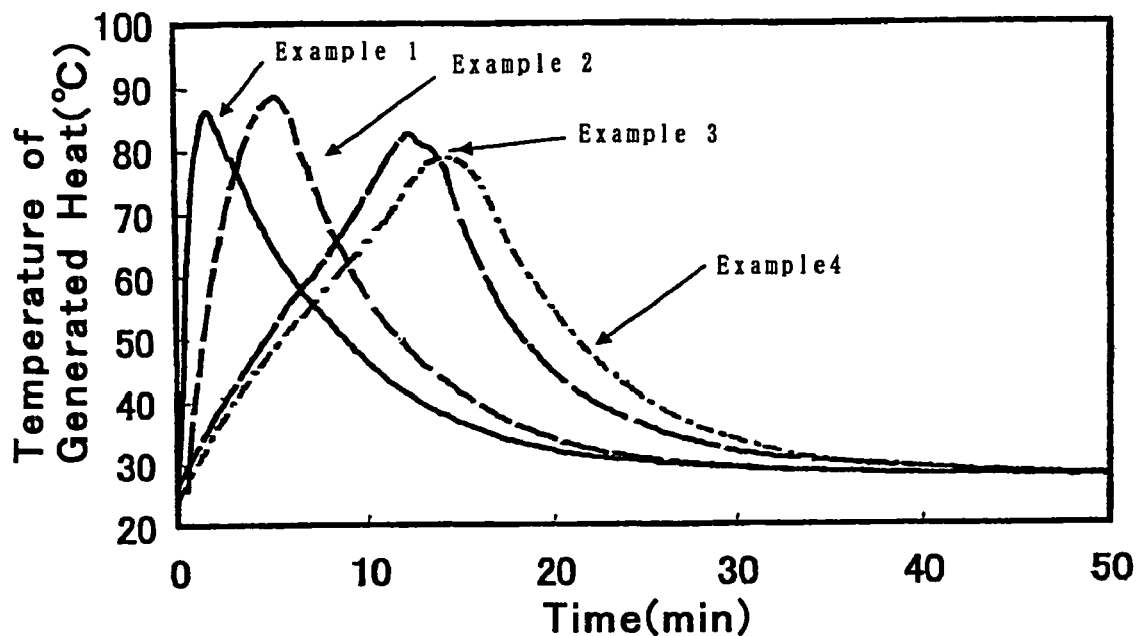
FIG. 1 is a graph showing the heat generation characteristics of heat generating molded articles obtained in Examples according to the present invention.

The present invention will be described with reference to its preferred embodiments by way of the accompanying drawings.

The process of the present invention starts with a papermaking step in which an intermediate product is formed from a raw material composition containing at least an oxidizable metal powder, a moisture retaining agent, a fibrous material, and water.

The oxidizable metal powder contained in the raw material composition includes any oxidizable metal powders commonly used in heat generating molded articles, such as iron powder, aluminum powder, zinc powder, manganese powder, magnesium powder, and calcium powder. Iron powder is preferred of them for its handling properties, safety, and production cost. From the standpoint of fixability to a fibrous material and ease of reaction control, it is preferred to use an oxidizable metal powder having a particle size of 0.1 to 300 µm. The term "particle size" as used herein means a maximum length of powder particles. It is more preferred to use powder containing those particles having a particle size of 0.1 to 150 µm in a proportion of 50% by weight or more.

The oxidizable metal powder content is preferably 10 to 90% by weight, more preferably 30 to 80% by weight, based on the raw material composition exclusive of water. With the oxidizable metal powder content lower than 10% by weight, the resulting heat generating molded article tends to fail to exhibit a substantial rise in temperature. Where the oxidizable metal powder content exceeds 90% by weight, the powder can fall off or impair the air permeability of the resulting molded article.

The moisture retaining agent contained in the raw material composition includes any moisture retaining agents commonly employed in heat generating molded articles. The moisture retaining agent not only serves for moisture retention but functions as an agent for holding and supplying oxygen to the oxidizable metal powder. Useful moisture retaining agents include activated carbon (palm shell charcoal, wood charcoal, bituminous coal, peat, lignite), carbon black, acetylene black, graphite, zeolite, pearlite, vermiculite, and silica. Preferred of them is activated carbon for its moisture retaining ability, oxygen supplying ability, and catalytic ability. It is preferred to use a moisture retaining agent having a particle size of 0.1 to 500 µm, particularly the one containing those particles with a particle size of 0.1 to 200 µm in a proportion of 50% by weight or more, in view of the capability of providing an effective contact with the oxidizable metal powder.

The moisture retaining agent is preferably present in an amount of 0.5 to 60% by weight, more preferably 1 to 50% by weight, based on the weight of the raw material composition exclusive of water. At a moisture retaining agent content lower than 0.5% by weight, the resulting molded article may fail to hold a requisite water content for sustaining the oxidation reaction. A moisture retaining agent content higher than 60% by weight can result in an increased heat capacity for the amount of heat generated only to give a small rise in temperature.

The fibrous material contained in the raw material composition includes any fibrous materials, whether natural or synthetic, with no particular restriction. The natural fibrous materials include plant fibers, e.g., cotton, kapok, wood pulp, non-wood pulp, peanut protein fiber, corn protein fiber, soybean protein fiber, mannan fiber, rubber fiber, linen, Manila hemp, sisal hemp, New Zealand hemp, Luo Buma, coconut fiber, rush, and straw; animal fibers, such as wool, goat hair (including mohair and cashmere), alpaca, angora, camel, vicuna, silk, down, small feather, alginate fiber, chitin fiber, and casein fiber; and mineral fibers, such as asbestos. The synthetic fibers include semi-synthetic ones, such as cellulose diacetate fiber, cellulose triacetate fiber, oxidized acetate fiber, promix fiber, chlorinated rubber, and rubber hydrochloride; synthetic polymer fibers, such as nylon, aramid, polyvinyl alcohol, polyvinyl chloride, polyvinylidene chloride, polyester (e.g., polyethylene terephthalate), polyacrylonitrile, acrylic polymers, polyethylene, polypropylene, polystyrene, polyurethane, rayon, viscous rayon, and cuprammonium rayon; metal fibers, carbon fiber, and glass fiber. Recycled products of these fibers are also employable. Preferred of them are wood pulp, cotton, and polyester from the viewpoint of capabilities of fixing powders present in the raw material composition thereto, flexibility of the resulting heat generating molded article, voids-dependent oxygen permeability, production cost, and the like. It is preferred for the fibrous material to have an average fiber length of 0.1 to 50 mm, more preferably 0.2 to 20 mm. Where the fiber length is too short, the resulting heat generating molded article tends to have insufficient strength. Too long fiber has reduced dispersibility in water, tending to result in a failure to provide a heat generating molded article with uniform thickness.

The content of the fibrous material in the raw material composition is preferably 2 to 80% by weight, more preferably 5 to 50% by weight, based on the weight of the composition exclusive of water. A fibrous material content less than 2% by weight can fail to hold the other components, including the oxidizable powder, of the raw material composition, causing the components to fall off. Where the fibrous material content is more than 80% by weight, the heat generating molded article will have an increased heat capacity for the amount of heat generated, and a reduced rise in temperature can result.

In the present invention, since the raw material composition is free from an electrolyte, which functions as an oxidation assistant, as mentioned above, the suspension has a lower ion concentration. It follows that the oxidizable metal powder exhibits improved dispersibility in the raw material composition. The oxidizable metal powder and the fibrous material are brought into substantial contact in the step of the suspension preparation. The oxidizable metal powder can thus be fixed to the surface of the fibrous material uniformly. As a result, the resulting heat generating molded article exhibits improved heat generation characteristics.

The raw material composition can further contain other additives generally used in paper manufacturing with no particular restrictions in addition to the aforesaid oxidizable metal, fibrous material, and moisture retaining agent. Such additives include sizings, colorants, strengthening agents, retention improvers, loading fillers, thickeners, pH control agents, and bulking agents. The amounts of the additives to be added can be selected appropriately according to the kinds.

The raw material composition thus prepared is subjected to papermaking process to make an intermediate product of desired shape.

An intermediate product can be made by any papermaking techniques conventionally used in the manufacture of pulp molded products of various shapes including sheets and three-dimensional articles. For example, papermaking techniques for preparing an intermediate product of sheet form include continuous papermaking by use of a cylinder paper machine, a foundrinier paper machine, a short-wire paper machine, a twin-wire paper machine, etc.; and batch papermaking such as manual papermaking. Papermaking techniques for preparing a three-dimensional intermediate product include a so-called injection method described, e.g., in Japanese Patent 3155522 (page 2, col. 4, line 17 to page 4, col. 8, line 23), a so-called core papermaking method described, e.g., in Japanese Patent 3155503 (page 2, col. 4, line 4 to page 4, col. 7, line 6), and a so-called in-water joining method described, e.g., in Japanese Patent 3072088 (page 2, col. 4, line 4 to page 3, col. 5, line 43). It is possible to additionally deposit the fibrous material on the surface of the intermediate product in the papermaking step.

It is desirable that the intermediate product should be dewatered to reduce its water content preferably to 70% (by weight, hereinafter the same) or less, more preferably to 60% or less, so as to retain its shape and to exhibit mechanical strength. An appropriate method of dewatering is chosen according to the shape of the intermediate product and the papermaking process adapted. For example, a sheet-shaped intermediate product can be dewatered by suction, blowing pressurizing air, or pressing with a pressure roll or a pressure plate. An intermediate product made by using a papermaking mold can be dewatered by, for example, blowing pressurizing air to the intermediate product in the mold or pressing the intermediate product onto the inner wall of the mold.

It is preferred that the intermediate product should be dried in a stage after papermaking (after dewatering where the process involves the above-mentioned dewatering step) and before incorporation of an electrolyte (described later). To carry out the drying step brings about the following advantages. (1) The intermediate product containing the oxidizable metal powder, which has thermal reactivity in an oxidizing atmosphere, is made to dry positively to reduce its water content to a prescribed level in a short time. As a result, the oxidizable metal powder is prevented from oxidation during the production of molded articles. (2) After drying, the fibrous material has increased capability of retaining the oxidizable metal powder and thereby prevents the powder from falling off. (3) The dried intermediate product or the final product after incorporating an electrode (described infra) has improved mechanical strength.

The temperature of drying the intermediate product in the drying step is preferably 60 to 300° C., more preferably 80 to 250° C. At drying temperatures lower than 60° C., it will take much time to regulate the water content of the intermediate product, and oxidation of the oxidizable metal powder may be induced meanwhile. At temperatures exceeding 300° C., the water content inside the intermediate product is apt to evaporate steeply to destroy the structure of the intermediate product.

The water content of the intermediate product after the drying step is preferably 60% or lower, more preferably 10% or lower. An intermediate product with water content more than 60% tends to be difficult to handle or requires an extra step for water content adjustment afterward, which impairs the productivity.

The manner of drying the intermediate product is chosen properly according to the shape of the intermediate product, the processing history of the intermediate product, the water content of the undried intermediate product, desired water content of the dried intermediate product, and like factors. For instance, the drying step is effected by (a) bringing the intermediate product into contact with a heating structure (heat generating element), (b) blowing heated air or steam (superheated steam), (c) drying in vacuo, (d) electromagnetic wave heating or (e) electric heating. The drying step and the aforementioned dewatering step may be carried out simultaneously.

Molding the intermediate product is preferably conducted in an inert gas atmosphere. If desired, the molding may be carried out in a usual air atmosphere because the intermediate product is free from an electrolyte acting as an oxidation assistant. In this case, the production equipment can be simplified. If necessary, the intermediate product can be subjected to fabricating steps such as trimming and altering the shape by some processing.

After the papermaking step, an electrolyte is incorporated into the intermediate product. This step is preferably performed in an inert gas atmosphere, such as nitrogen or argon. In case where the intermediate product has been dried positively to reduce its water content as described above, an electrolyte solution can be added in a usual air atmosphere because oxidation is suppressed from proceeding abruptly immediately after addition of the electrolyte solution. Any of electrolytes that have been generally used in heat generating molded articles can be incorporated into the intermediate product. Useful electrolytes include sulfates, carbonates, chlorides or hydroxides of alkali metals, alkaline earth metals or heavy metals. Inter alia, chlorides including sodium chloride, potassium chloride, calcium chloride, magnesium chloride, and iron (II) or (III) chloride are preferred for their high electrical conductivity and excellent chemical stability and from the standpoint of production cost.

The method of incorporating the electrolyte into the intermediate product is selected appropriately depending on the treatment given to the intermediate product after papermaking and the water content and form of the intermediate product. The electrolyte can be incorporated into the intermediate product by, for example, impregnating the intermediate product with a solution of the electrolyte having a prescribed concentration or feeding the electrolyte in a solid form with a prescribed particle size. In order to distribute the electrolyte throughout the intermediate product uniformly while adjusting the water content, the impregnation method using an electrolyte solution of a given concentration is preferred.

When the intermediate product is impregnated with an electrolyte solution, the manner of impregnation is chosen appropriately according to the shape and water content of the intermediate product. For example, impregnation can be achieved by applying an electrolyte solution to the intermediate product by spraying, brush coating, dip coating, gravure coating, reverse coating, doctor blade coating, etc. Spraying would be preferred from the standpoint of uniformity of application, ease and simplicity of operation, and relatively low cost for coating equipment.

After the intermediate product is provided with the electrolyte, the water content of the intermediate product is adjusted and stabilized if necessary. The resulting heat generating molded article can be fabricated further by trimming, laminating, and the like to obtain a final product of desired size.

Where the heat generating molded article thus obtained has a sheet form, it has a thickness of 0.1 to 10 mm and a basis weight of 50 to 5,000 g/m$^2$ and exhibits satisfactory heat generation characteristics as exemplified by a highest reached temperature of 30 to 150° C.

The resulting heat generating molded article can be covered with a cover that is permeable to oxygen over the entire area thereof or in part thereof. The cover may be of any material having air permeability. The cover is provided by superposing, on the heat generating molded article, paper, nonwoven fabric, a microporous film, a finely perforated resin film, etc. or by coating or impregnating the heat generating molded article with a synthetic resin coating, an emulsion coating, etc.

The heat generating molded article is supplied to the market in oxygen impermeable and moisture impermeable packages so as to be kept away from oxygen until use.

As described above, the process according to the present invention makes it possible to easily control the electrolyte content and the water content of the resulting heat generating molded article. The process minimizes oxidation of an oxidizable metal during the production of a heat generating molded article. Thus, the process provides a heat generating molded article with satisfactory heat generation characteristics.

The present invention is by no means limited to the above-described embodiments, and various changes and modifications can be made therein without departing from the spirit and scope thereof.

The process according to the present invention is effective to the production of not only heat generating molded articles of sheet form but those having a three-dimensional shape.

In Examples 1 to 4 and Comparative Examples 1 to 3 hereinafter given, heat generating molded articles were produced under the conditions described and evaluated for heat generation characteristics in terms of temperature reached when they were let to generate heat on an expanded polystyrene plate in air at 25° C. and 50% RH. The heat generation characteristics measured in Examples and Comparative Examples are graphically represented in FIGS. 1 and 2, respectively.

EXAMPLES 1 TO 4

1. Raw Material Composition (Stock)

| | |
|---|---|
| Oxidizable metal powder: iron powder (average particle size: 45 μm) | 15 g |
| Fibrous material: pulp fiber (average fiber length: 1.3 mm) | 2.25 g |
| Moisture retaining agent: activated carbon (average particle size: 40 μm) | 7.5 g |
| Water: distilled water | 500 ml |

2. Electrolyte Solution
   Electrolyte: NaCl
   Water: distilled water
   Electrolyte concentration: 10 wt %

3. Papermaking Conditions

The stock was screened through a manual papermaking device having a 100 mesh screen of 170 mm in diameter to deposit a fiber layer on the mesh.

4. Dewatering Conditions

The fiber layer as deposited on the screen was dewatered by suction for 1 minute to obtain an intermediate product with a water content of 70%.

5. Drying Conditions

The resulting intermediate product was pressed on a hot press under a pressure of 1.96 MPa for 40 seconds while being heated to dry to obtain an intermediate product of sheet form (water content: 2%).

6. Form of Intermediate Product

The intermediate product was 2.7 to 2.8 mm in thickness and 990 to 1050 g/m² in basis weight.

7. Addition of Electrolyte Solution

A 50 mm by 50 mm piece was cut out of the resulting intermediate product. The cut piece was sprayed with the electrolyte solution in a nitrogen atmosphere to obtain a heat generating molded article, of which the electrolyte solution content and water content are shown in Table 1 in terms of part by weight per 100 parts by weight of the intermediate product.

COMPARATIVE EXAMPLES 1 TO 3

A fiber layer was formed in the same manner as in Examples 1 to 4, except for using a stock prepared by adding 25 g of NaCl to the stock used in Examples 1 to 4. The fiber layer was dehydrated under the conditions shown in Table 1 to obtain a heat generating molded article. The resulting molded article had a thickness of 2.8 to 2.9 mm and a basis weight of 2010 to 2280 g/m².

Figure 2:
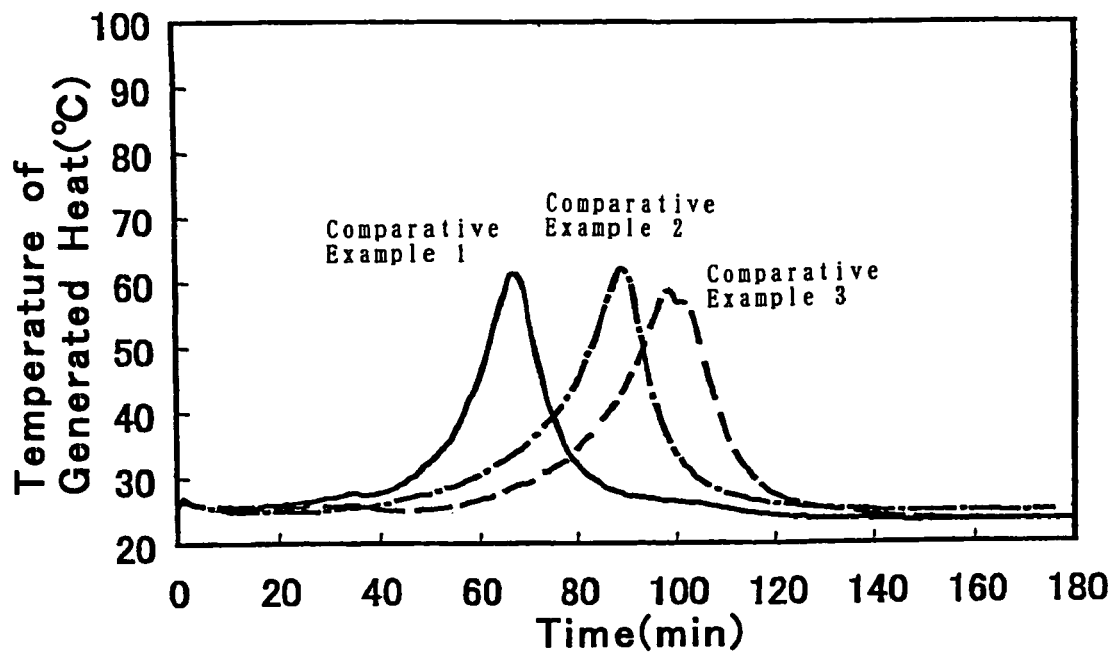
FIG. 2 is a graph showing the heat generation characteristics of heat generating molded articles obtained in Comparative Examples.

The heat generating molded articles of Examples 1 to 4 can have adjusted electrolyte content and water content by varying the amount of the electrolyte solution added and accordingly, as can be confirmed from FIG. 1, exhibit broadly ranging heat generation characteristics in terms of temperature reached and rate of temperature rise. All the heat generating molded articles of Examples were proved to reach sufficiently high temperatures on heat generation. In contrast, the heat generating molded articles obtained in Comparative Examples 1 to 3 have a water content in a narrow range of from 51 to 54% even if the pressing force or pressing time in the dehydration step are changed. That is, the water content is adjustable only in a limited range. As shown in FIG. 2, the comparative molded articles were inferior to the products of Examples in heat generation characteristics, i.e., the temperature rise was slower, and the reached temperature was lower.

TABLE 1

| | | Example | | | | Comparative Example | | |
|---|---|---|---|---|---|---|---|---|
| | | 1 | 2 | 3 | 4 | 1 | 2 | 3 |
| Stock Composition (g) | Iron Powder | | | | 15 | | | |
| | Activated Carbon | | | | 7.5 | | | |
| | Pulp | | | | 2.25 | | | |
| | Water | | | | 500 | | | |
| | NaCl | | | 0 | | | 25 | |
| Dewatering/ dehydration Condition | Suction | | | | yes | | | |
| | Pressing Force (MPa) | | | — | | | 1.96 | |
| | Temp. (°C.) | | | — | | 25 | 25 | 25 |
| | Time (sec) | | | — | | 40 | 90 | 300 |
| | Resulting Water Content % | | | 70 | | 52 | 51 | 54 |
| Drying Condition | Pressing Force (MPa) | | | 1.96 | | | — | |
| | Temp. (°C.) | | | 200 | | | — | |
| | Time (sec) | | | 40 | | | — | |
| | Resulting Water Content | | | 2 | | | — | |
| Elelctrolyte Adding Condition | Amount of 10% NaCl Solution Sprayed (part) | 40 | 70 | 100 | 120 | — | | |
| | Final Water Content (%) | 27 | 38 | 46 | 50 | 52 | 51 | 54 |

INDUSTRIAL APPLICABILITY

According to the present invention, the electrolyte content and the water content of a heat generating molded article can easily be controlled, oxidation of an oxidizable metal during the production can be minimized, and a heat generating molded article exhibiting satisfactory heat generation characteristics can therefore be obtained.

The invention claimed is:

1. A process of producing a heat generating molded article, which comprises:
   making an intermediate shaped product by a papermaking process from a raw material composition comprising at least
     from 30 to 90 wt. % based on the weight of the raw material composition exclusive of water of an oxidizable metal powder having a particle size of 0.1 to 300 μm,
     from 0.5 to 60 wt. % based on the weight of the raw material composition exclusive of water of activated carbon,
     from 2 to 80 wt. % based on the weight of the raw material composition exclusive of water of a fibrous material, and
     water and
   incorporating an electrolyte into the resulting intermediate product, and
   fabricating a heat generating molded article.

2. The process according to claim 1, which further comprises: drying the intermediate shaped product before incorporating the electrolyte.

3. The process according to claim 2, wherein incorporating the electrolyte is carried out by impregnating the intermediate shaped product with a solution of the electrolyte.

4. The process according to claim 2, wherein said intermediate shaped product is dried to a water content of 10% or lower.

5. The process according to claim 1, wherein said incorporating the electrolyte is carried out by impregnating the intermediate shaped product with a solution of the electrolyte.

6. The process according to claim 1, wherein said oxidizable metal powder comprises at least one selected from the group consisting of iron powder, aluminum powder, zinc powder, manganese powder, magnesium powder and calcium powder.

7. The process according to claim 1, wherein said oxidizable metal powder comprises iron powder.

8. The process according to claim 1, wherein a content of said oxidizable metal powder content is 30 to 8% by weight based on the raw material composition exclusive of water.

9. The process according to claim 1, wherein a content of said oxidizable metal powder having a particle size of 0.1 to 150 μm is 50% by weight or more.

10. The process according to claim 1, wherein said activated carbon has a particle size of 0.1 to 500 μm.

11. The process according to claim 1, wherein a content of said activated carbon having a particle size of 0.1 to 200 μm is 50% by weight or more.

12. The process according to claim 1, wherein a content of said activated carbon is from 1 to 50 wt. % based on the weight of the raw material composition exclusive of water.

13. The process according to claim 1, wherein said fibrous material has an average fiber length of 0.1 to 50 mm.

14. The process according to claim 1, wherein a content of said fibrous material is 5 to 50 wt. % based on the weight of the raw material composition exclusive of water.

15. The process according to claim 1, wherein said raw material composition is free from an electrolyte.

16. The process according to claim 1, wherein said step of incorporating an electrolyte is performed in an inert gas atmosphere.

* * * * *

UNITED STATES PATENT AND TRADEMARK OFFICE
CERTIFICATE OF CORRECTION

PATENT NO. : 7,625,464 B2  Page 1 of 1
APPLICATION NO. : 10/490120
DATED : December 1, 2009
INVENTOR(S) : Matsui et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 742 days.

Signed and Sealed this

Twenty-first Day of December, 2010

David J. Kappos
*Director of the United States Patent and Trademark Office*